United States Patent [19]

Demler et al.

[11] 4,358,410
[45] Nov. 9, 1982

[54] PROCESS FOR THE PREPARATION OF META SULFOBENZOIC ACID AND META HYDROXYBENZOIC ACID THEREFROM

[75] Inventors: Walter R. Demler; David M. Todoroff, both of Hamburg, N.Y.

[73] Assignee: Buffalo Color Corporation, West Paterson, N.J.

[21] Appl. No.: 299,984

[22] Filed: Sep. 8, 1981

[51] Int. Cl.³ .................... C07C 143/52; C07C 65/03
[52] U.S. Cl. ................................. 260/507 R; 562/475
[58] Field of Search .................... 260/507 R; 562/475

[56] References Cited

U.S. PATENT DOCUMENTS 3,094,558  6/1963  Strojay et al. ...................... 562/475

*Primary Examiner*—Nicky Chan
*Attorney, Agent, or Firm*—Michael L. Dunn

[57] ABSTRACT

A process for the preparation of meta sulfobenzoic acid wherein after solution sulfonation of benzoic acid, meta sulfobenzoic alkali metal salt is precipitated by treating the solution with an alkali metal salt at a temperature below about 120° C. The precipitate is then filtered from the solution and rinsed at least once with a cold rinse solution containing from 3 to 10 percent of an alkali metal salt The resulting product has a lower concentration of alkali metal salt, usually sodium chloride, than was obtained using prior art methods. The product is especially suitable for use in a process to manufacture m-hydroxy benzoic acid.

8 Claims, No Drawings

PROCESS FOR THE PREPARATION OF META SULFOBENZOIC ACID AND META HYDROXYBENZOIC ACID THEREFROM

BACKGROUND OF THE INVENTION (A) Field of the Invention

This invention relates to the preparation of meta sulfobenzoic acid (m-sulfobenzoic acid) and meta hydroxybenzoic acid (m-hydroxybenzoic acid) therefrom and more particularly relates to a process for the isolation of m-sulfobenzoic acid from a sulfonation reaction mixture.

(B) History of the Prior Art

It has been known in the prior art that m-sulfobenzoic acid can be prepared by sulfonation of benzoic acid with fuming sulfuric acid or sulfur trioxide (see e.g., U.S. Pat. No. 3,094,558; Justus Liebig's Annalen Der Chemie, Vol. 280, pg. 6, 1894 by Kekule et al.; Journal of the American Chemical Society, 1932, beginning at pg. 2009 and "Sulfonation and Sulfation with Sulfur Trioxide", Gilbert et al., Industrial Engineering Chemistry, (1953), pp. 2065–2072.

In such prior art preparations of m-sulfobenzoic acid, the reaction mass was generally dissolved in cold water, usually filtered and the sulfobenzoic acid was salted out with a high sodium chloride salt concentration to precipitate the benzene sulfonate. The crude sulfobenzoic acid was then frequently washed with saturated salt solution which was sometimes cold. The product was then pressed to remove excess water containing the sodium chloride.

Such processes for isolating the m-sulfobenzoic acid were very complicated, often resulted in loss of yield and resulted in products which had a high sodium chloride salt contamination. It was, however, believed that the high sodium chloride concentrations were essential both for salting out and washing purposes in order to prevent large losses of product by means of its solubility in the wash liquid. The resulting m-sulfobenzoic acid products contained high sodium chloride and sometimes contained substantial residual sulfates or bi-sulfates which seem to interfere with the preparation of high quality m-hydroxybenzoic acid from the m-sulfobenzoic acid by fusion of the m-sulfobenzoic acid with alkali metal hydroxide.

BRIEF DESCRIPTION OF THE INVENTION

In accordance with the present invention, there is provided a process for the preparation of m-sulfobenzoic acid by solution sulfonation of benzoic acid wherein the resulting m-sulfobenzoic acid is isolated from the reaction mass by an improved process step. The improvement comprises precipitating the m-sulfobenzoic acid alkali metal salt from the sulfonation solution by treating the solution with sufficient alkali metal chloride salt to cause essentially all m-sulfobenzoic acid in the sulfonation solution to precipitate as m-sulfobenzoic acid salt at a temperature below about 12° C. After the m-sulfobenzoic acid salt precipitates, it is filtered from the solution to form a wet cake. The wet cake is then rinsed at least once with a cold rinse solution containing from 3 to 10% of an alkali metal chloride salt. From about 100 to about 1000 milliliters of such alkali metal chloride salt solution per rinse is used per kilogram of m-sulfobenzoic acid alkali metal salt in the wet cake. The resulting m-sulfobenzoic acid contains a low concentration of inorganic sulfates and sulfonates and contains a much lower concentration of sodium chloride than was obtained using prior art methods. The m-sulfobenzoic acid isolated in accordance with the present invention appears to be better suited for the preparation of m-hydroxy benzoic acid by alkali metal hydroxide fusion of the corresponding m-sulfobenzoic acid.

The process of the invention is much less complicated than prior art methods, has lower sodium chloride salt concentration and product loss by solution in the rinse liquid is minimal.

DETAILED DESCRIPTION OF THE INVENTION

The improvement in the process of the invention comprises precipitating m-sulfobenzoic acid alkali metal salt from the sulfonation solution by treating the solution with sufficient alkali metal chloride salt to cause essentially all m-sulfobenzoic acid in the solution to precipitate at the precipitating temperature. "Essentially all", as used herein, means that less than about 5% m-sulfobenzoic acid remains in solution. In general, the salt concentration used is a concentration such that the sulfonation solution becomes saturated with sodium chloride salt. The temperature to precipitate essentially all m-sulfobenzoic acid salt from the sulfonation solution (precipitating temperature) is a temperature below about 12° C. but above the freezing temperature of the sulfonation solution. The precipitating temperature is usually between about 2° C. and about 12° C.

The precipitated m-sulfobenzoic acid alkali metal salt is filtered from the solution by any suitable means. The filtered precipitate is in the form of a wet cake prior to drying and in accordance with the invention, is then rinsed at least once with a rinse solution containing from 3 to 10 and preferably from about 4 to about 7 percent of an alkali metal chloride salt at a temperature of below about 12° C. It has been unexpectedly discovered that the combination of a 3 to 10 percent alkali metal chloride salt solution and low temperature permit rinsing of the m-sulfobenzoic acid salt precipitate without substantial loss of the precipitate to solution. It was previously believed that very high salt concentrations were required to prevent dissolving of the desired precipitate. As previously discussed, from about 100 to about 1000 milliliters and preferably from about 100 to about 250 milliliters of the alkali metal chloride salt rinse solution are used per rinse per kilogram of m-sulfobenzoic acid alkali metal salt in the wet cake.

Multiple rinses may be used if desired. For example, after the first rinsing of the wet cake, the wet cake may again be rinsed with an additional from about 100 to about 1000 milliliters of a second rinse solution per kilogram of m-sulfobenzoic acid alkali metal salt in the wet cake. The second rinse solution also contains from about 3 to about 10 weight percent of alkali metal chloride salt. The preferred alkali metal chloride salt concentration in the rinse solution or solutions is from about 4 to about 7 weight percent. The alkali metal chloride is almost always sodium or potassium chloride and is usually sodium chloride. The first and second rinse solutions may contain the same alkali metal chloride salt concentrations. Rinse solution temperature is usually between about 2° C. and 12° C.

More than three rinses are usually avoided since m-sulfobenzoic acid product loss increases with the number of rinses and total volume of rinse solution used.

As can be seen from the foregoing discussion, the isolation procedure in accordance with the present invention to separate m-sulfobenzoic acid from its sulfonating liquid, without retaining large amounts of inorganic salt, is uncomplicated.

The following example serves to illustrate and not limit the present invention. Unless otherwise indicated, all parts and percentages are by weight.

EXAMPLE 4 moles of benzoic acid is melted at 125° to 130° C. in a two liter flask. 1621 grams of 20% oleum is then added at a temperature of from 125° to 140° C. The reaction mass is then held for one hour at 130° C. The reaction mass is then split into 2 parts, A and B, each of which is dissolved in about 3000 mls of saturated NaCl salt solution over a period of 40 minutes. The solution is then heated to from 80° to 85° C. The solution is then allowed to cool to 50° C. and is then agitated and further cooled to 8°–12° C. with an ice bath. Part A was then washed twice with 250 mls of 5% NaCl solution at 5° C. and Part B was washed twice with 250 mls of 25% NaCl solution at 5° C. Part A, washed in accordance with the present invention is found by U.V. to have a 95% strength. Part B is found to have a 78.2% strength. The yield in both cases is about 90%.

What is claimed is:

1. In a process for the preparation of m-hydroxy benzoic acid by solution sulfonation of benzoic acid to form m-sulfobenzoic acid followed by fusing the m-sulfobenzoic acid salt with alkali metal hydroxide and hydrating the resulting m-hydroxy benzoic acid alkali metal salt to form m-hydroxy benzoic acid, the improvement which comprises: precipitating m-sulfobenzoic acid alkali metal salt from the sulfonation solution by treating the solution with sufficient alkali metal chloride salt to cause essentially all m-sulfobenzoic acid in the sulfonation solution to crystallize as m-sulfobenzoic acid salt at a temperature below about 12° C.; filtering the precipitate from the solution to form a wet cake; and rinsing the wet cake at least once with a cold rinse solution containing from 3–10 percent of an alkali metal chloride salt, from about 100 to about 1000 milliliters of said alkali metal chloride salt solution being used per kilogram of m-sulfobenzoic acid alkali metal salt in said wet cake.

2. The process of claim 1 wherein the rinse solution contains from about 4 to about 7 weight percent of sodium chloride salt.

3. The process of claim 1 wherein after rinsing the wet cake, the wet cake is again rinsed with from about 100 to about 1000 milliliters of a second rinse solution, per kilogram of m-sulfobenzoic acid alkali metal salt in the wet cake, the second rinse solution also containing from about 3 to about 10 weight percent of an alkali metal chloride salt.

4. The process of claim 3 wherein both rinse solutions contain from about 4 to about 7 weight percent of sodium chloride salt.

5. The process of claim 3 wherein both rinse solutions contain the same concentration of alkali metal chloride salt.

6. The process of claim 1 wherein the rinse solution has a temperature of from about 2° to about 12° C.

7. The process of claim 4 wherein the rinse solution has a temperature of from about 2° to about 12° C.

8. In a process for the preparation of m-sulfobenzoic acid by solution sulfonation of benzoic acid, the improvement which comprises: precipitating m-sulfobenzoic acid alkali metal salt from the sulfonation solution by treating the solution with sufficient alkali metal chloride salt to cause essentially all m-sulfobenzoic acid in the sulfonation solution to precipitate as m-sulfobenzoic acid salt at a temperature below about 12° C.; filtering the precipitate from the solution to form a wet cake; and rinsing the wet cake at least once with a cold rinse solution containing from 3–10 percent of an alkali metal chloride salt at below about 12° C. from about 100 to about 1000 milliliters of said alkali metal chloride salt solution being used per rinse per kilogram of m-sulfobenzoic acid alkali metal salt in said wet cake.

* * * * *